United States Patent [19]

Liegner

[11] Patent Number: 4,803,999
[45] Date of Patent: Feb. 14, 1989

[54] CATHETER SYSTEM

[76] Inventor: Kenneth B. Liegner, 8 Barnard Rd., Armonk, N.Y. 10504

[21] Appl. No.: 147,784

[22] Filed: Jan. 25, 1988

Related U.S. Application Data

[63] Continuation-in-part of Ser. No. 321,696, Nov. 16, 1981, abandoned, which is a continuation of Ser. No. 77,396, Sep. 20, 1979, abandoned.

[51] Int. Cl.$^4$ ............................................. A61B 5/00
[52] U.S. Cl. ............................... 128/763; 604/169; 604/256; 604/264
[58] Field of Search ............... 128/752, 753, 763, 766, 128/DIG. 26; 604/164–170, 249, 256, 264

[56] References Cited

U.S. PATENT DOCUMENTS

| | | | |
|---|---|---|---|
| 1,103,967 | 7/1914 | Hughes | 604/264 |
| 2,893,395 | 7/1959 | Buck | 604/283 |
| 3,572,333 | 3/1971 | Hubert | 604/170 |
| 3,707,972 | 1/1973 | Villari et al. | 604/249 |
| 3,799,172 | 3/1974 | Szpur | 604/249 |
| 3,811,440 | 5/1974 | Moorehead et al. | 604/169 |
| 3,977,400 | 8/1976 | Moorehead | 604/169 |
| 4,149,535 | 4/1979 | Volder | 604/164 |

Primary Examiner—Max Hindenburg
Attorney, Agent, or Firm—Kane, Dalsimer, Sullivan, Kurucz, Levy, Eisele and Richard

[57] ABSTRACT

Improved catheter system particularly adapted for multiple blood sample comprises a cannula defining a lumen having a side opening intermediate its ends, and an obturator slidably insertable in the lumen, the obturator being movable in the lumen between a first position wherein its proximal end extends proximally of the side opening and a second position wherein its proximal end terminates distally of the side opening. The side opening includes a tulip-shaped extension to permit the complete and efficient cleansing of the opening between multiple samplings of blood. Means for adapting the catheter system for continuous intravenous therapy are also disclosed.

11 Claims, 2 Drawing Sheets

CATHETER SYSTEM

BACKGROUND OF THE INVENTION

CROSS-REFERENCE TO RELATED APPLICATIONS

This application is a continuation-in-part of pending U.S. patent application Ser. No. 321,696 filed Nov. 16, 1981 and which is a continuation of the U.S. patent application Ser. No. 077,396 filed Sept. 20, 1979 and both now abandoned.

FIELD OF THE INVENTION

This invention pertains to catheters and more particularly to catheter systems suitable for multiple blood sampling.

DESCRIPTION OF THE PRIOR ART

Oftentimes patients require multiple blood sampling. Such patients are generally subjected to repeated venipunctures which are not only painful but may also lead to damage of veins and the surrounding tissue. To avoid this problem, others have suggested retaining the catheter in the patient to accommodate repeated intravenous or intra-arterial access.

In one known arrangement, a venipuncture needle is inserted through an open-ended catheter into the patient. The needle is then withdrawn and replaced with an obturator which occludes the catheter. When sampling is desired, the obturator is fully removed whereupon a syringe or a similar device may be secured to the distal end of the catheter for sampling. After each sample is taken, the syringe is removed and the obturator reinserted. While this arrangement is an improvement over the prior art devices requiring repeated venipuncture to accommodate multiple sampling, it is disadvantageous insofar as it requires complete removal of the obturator before each sample is taken. Thus, each removal of the obturator is accompanied by some spillage of blood and possible contamination. Also known is the use of a flashback chamber at the distal end of the needle for providing a visual indication of successful venipuncture.

Other catheter systems, none of which provides a simple solution to the problem of multiple blood sampling, are disclosed in U.S. Pat. Nos. 958,854; 4,037,600; 3,081,770; 3,645,253; 3,717,151; 3,734,080; 3,817,240; 3,886,930; 3,931,815; 3,937,220; 3,961,622 and 4,099,520.

SUMMARY OF THE INVENTION

According to the present invention, I have developed a catheter system particularly suited for multiple blood sampling, which avoids the necessity of repeated venipuncture and minimizes spillage of blood and the possibility of contamination associated therewith. The system is easy to use and sufficiently inexpensive to permit disposal after use on a single patient.

The catheter system comprises a cannula, a venipuncture needle and an obturator. The cannula is provided with a side opening intermediate its ends, preferably about one-third of the overall length from the distal end. A hub formed with a radially extending bore which communicates with the side opening in the cannula is secured about the distal end portion of the cannula. One mating part of a Luer-Lok or similar arrangement is formed about the bore, preferably integrally with the hub, to accommodate attachment of a syringe or the like which, for this purpose, is formed with the other mating part of the Luer-Lok at its attachment end. The preferred venipuncture needle defines a continuously extending longitudinal bore and is dimensioned for a sliding fit in the lumen of the cannula. A clear plastic hub defining a flashback chamber is secured to the distal end of the needle such that the flashback chamber communicates with the needle bore. The length of the needle is selected such that when the needle is fully inserted through the distal end of the cannula, the sharpened end of the needle protrudes slightly beyond the proximal end of the cannula. In this position, venipuncture is accomplished conventionally by simply inserting the sharpened end of the needle into the patient's vein, with successful insertion being indicated by the backflow of blood into the flashback chamber. After venipuncture is complete, the needle is removed and the cannula secured to the patient, as by taping. At this point, the obturator is inserted into the distal end of the cannula to occlude the lumen and block the further flow of blood thereby preventing the escape of blood both through the side opening and the distal end of the cannula. For this purpose, the obturator is preferably dimensioned for a close frictional sliding fit in the lumen of the cannula and has an enlarged distal end to facilitate handling. If desired, a sealing cap may be secured over the side opening during venipuncture to prevent the escape of blood through the side opening upon withdrawal of the needle.

In order to avoid blood clotting at the proximal end of the lumen, the overall length of the obturator is preferably selected such that when the obturator is fully received in the cannula, the proximal end of the obturator extends slightly beyond the proximal end of the cannula. Desirably, an additional Luer-Lok or the like is used for securing the obturator against distal movement from its fully inserted position.

When sampling is desired, a tourniquet is applied to the extremity and the syringe is secured via the Luer-Lok in the bore in the hub which communicates with the side opening of the cannula. At this point the obturator is withdrawn until its proximal end is located distally of the side opening. The syringe is then aspirated to withdraw blood through the side opening, flow through the distal end of the cannula being blocked by th proximal end of the obturator.

When sampling is completed, the tourniquet is released, the obturator is reinserted into the cannula to its full length and the syringe removed. When additional samples are desired, the tourniquet is reapplied whereupon the syringe is simply reattached and the obturator again partially withdrawn distally of the side opening. Of course, sterile techniques should be utilized during the initial venipuncture and subsequent samplings to avoid the possibility of contamination.

In addition to intravenous blood sampling, the device may be used as well for intra-arterial sampling, the principal advantage again being the reduction in the trauma which accompanies repeated arterial punctures. Also, while the device is particularly suited for multiple blood sampling, it may be readily modified to accommodate continuous intravenous therapy. For example, if the obturator is fully removed and a cap secured over the side opening to block flow through the distal end of the cannula. Alternatively, the distal end of the cannula may be blocked, as by a shortened obturator terminating distally of the side opening, and continuous intravenous therapy applied through the side opening.

A great advantage of the current invention is that it permits repeated access to the vascular system for multiple blood sampling without any blood or fluid filled spaces remaining during periods between sampling. Thus, there is no necessity for either "wasting" a specimen of blood prior to actual sampling or for instilling any heparin anticoagulant when sampling is completed. This is in contrast to prior art devices such as the so-called "Heparin Lock" system or the Sorenson "Intraflo" (used for arterial lines). Likewise there is no need for continuous connection to intravenous fluids nor pressurized arterial lines, thus the patient would be unemcumbered and free to move about without restriction.

The absence of blood or fluid filled spaces or recesses is important in maintaining the sterility of the system and minimizing the possibility of bacterial colonization or other contamination.

Further features and advantages of the catheter system according to the present invention will be more fully apparent from the following detailed description and annexed drawings of the preferred embodiments thereof.

DETAILED DESCRIPTION OF THE PREFERRED EMBODIMENTS OF THE INVENTION

Figure 1:
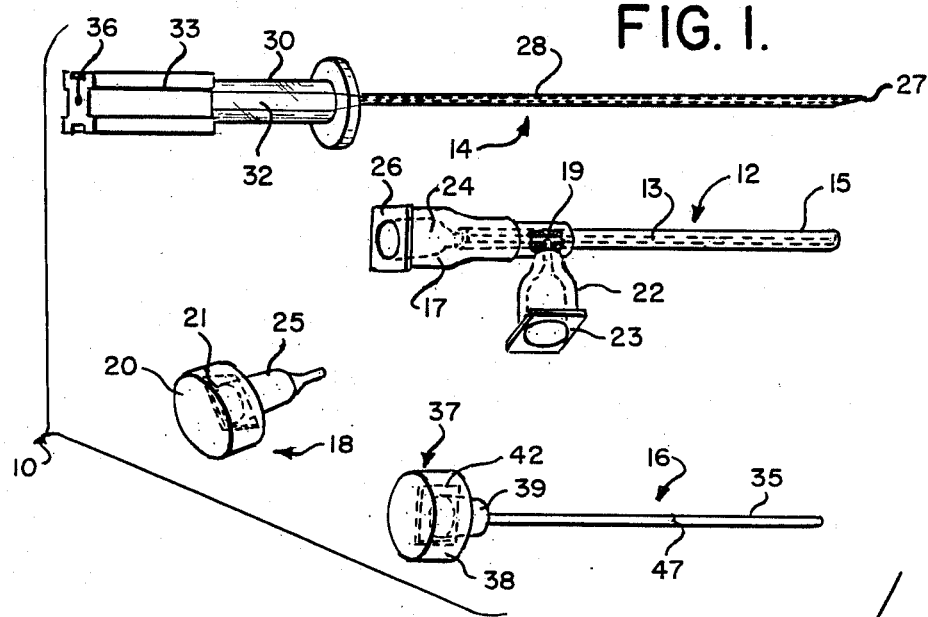
FIG. 1 is a perspective view of preferred components of the catheter system according to the present invention.

Referring now to the drawings, and initially to FIGS. 1-4 thereof, the preferred components of a catheter system according to the present invention are collectively designated by the reference numeral 10. As shown, the system 10 includes a cannula 12, a venipuncture needle 14, an obturator 16 and a sealing cap 18.

The cannula 12 defines a lumen 13 of preferably uniform diameter. The cannula includes an opening 19 intermediate its ends, preferably about one-third of the overall length from the distal end. A hub 17 is preferably secured about the distal end of the cannula 12. The hub 17 provides added structural integrity and includes means, such as a preferably integral tubular extension 22 having a flange 23 at its free end, for receiving a syringe or the like for communication with the opening 19. Preferably, the hub 17 is integrally formed and joined to the cannula 12 as by a suitable adhesive. For reasons that will be apparent hereinafter, the distal end of the hub 17 is formed with a widened bore 24 and an additional flange 26 which, like tubular extension 22, is adapted to receive a syringe or the like. The cannula 12 is preferably semi-rigid and, being intended for insertion into the patient's vascular system, should be comprised of a suitable physiologically inert material, with polytetrafluoroethylene being preferred. While the exact dimensions of the cannula are not critical, it preferably has an overall length of several inches and its proximal end 15 is desirably 16–23 gauge.

It may be advantageous for the catheter system to be optionally designed for cannula 12 and obturator 16 to have a gentle curve in one embodiment to facilitate comfortable placement in situ in the region of the antecubital fossae, conforming to the anatomy of the veins in this region.

Preferred needle 14 has a sharpened end 27 and a continuously extending bore 28. A hub 30 defining a flashback chamber 32 communicating with the bore 28 is preferably secured, as by a suitable adhesive, about the distal end of the needle 14. The hub 30 is preferably comprised of a suitable clear plastic whereby successful insertion of the needle into the patient's vein will be indicated by the backflow of blood into the flash back chamber 32. As usual, a cap 33 is secured about the distal end of the needle 14, the cap having a plug (not shown) which seats in the distal end of the flashback chamber 32 and a small axial thru-hole 36 to accommodate the escape of air from the chamber 32. The needle 14 is preferably dimensioned for a close fit in the lumen 13 to prevent the possibility of leakage between needle 14 and cannula 12. Needle 14 should be comprised of a suitable rigid material, such as metal or metal alloy, with steel being preferred. Hub 30 is preferably comprised of a suitable hard, clear plastic such as a polycarbonate resin. Cap 33 is preferably fabricated of polyethylene.

Figure 2:
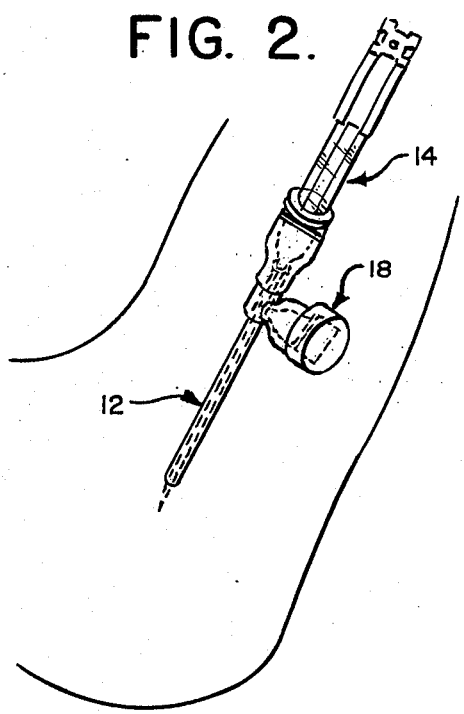
FIG. 2 is a perspective view of the needle and cannula as they appear during venipuncture.
Figure 4:
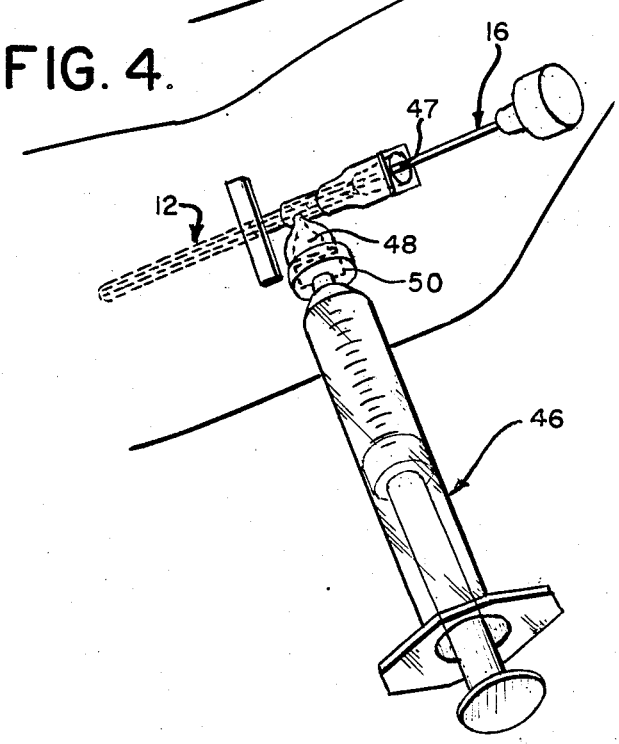
FIG. 4 is a perspective view showing the obturator in its partially withdrawn position which it assumes during sampling through the side opening.

Referring to FIG. 2, the length of the needle 14 should be selected such that when needle 14 is fully inserted into lumen 13, the sharpened end 27 of the needle will extend slightly beyond the proximal end of the cannula. With the needle thus disposed, venipuncture is accomplished by inserting the sharpened end 28 into the patient's vein. After the needle 14 is removed, the cannula 12 is preferably secured to the patient, as by taping (FIG. 3).

During the venipuncture procedure, the cap 18 is preferably secured over the free end of the tubular extension 22 thereby avoiding the possibility of leakage through the side opening 19. Preferred cap 18 is integrally formed and includes a plug 25 dimensioned for a close fit in the bore of the tubular extension 22 and an annular member 20 having internal projecting threads 21 formed about the distal end of the plug 25. To secure the cap 18 in place, the plug 25 is inserted into the bore of the tubular extension 22 until the flange 23 is in the annular region defined between the plug 25 and the annular member 20. If the cap 18 is then rotated, engagement between threads 21 and flange 23 serves to secure cap 18 in place. This arrangement for releasably mating axially aligned members is known in the art as a Luer-Lok. When fluid proof cap 18 is in place, the proximal end of the plug 25 preferably terminates at the defining wall of the lumen 13 thereby preventing the possible accumulation of blood and subsequent clotting in this space. Cap 18 is preferably comprised of a suitable plastic such as polytetrafluoroethylene.

Obturator 16 preferably includes a narrow portion 35 dimensioned for a frictional sliding fit in lumen 13, a plug 39 dimensioned for a close fit in bore 24, and a cap 37, the plug 39 and cap 37 being adhesively or otherwise secured about the distal end of the narrow portion 35. Since the obturator is inserted into the blood flow path, it too should be comprised of a physiologically inert material, polytetrafluoroethylene again being preferred. The obturator 16 by its sliding fit in the lumen 13, eliminates all recesses in the blood flow path, in which blood or blood debris can accumulate. The obturator 16 also functions as a valve to open and close sideport 19.

Figure 3:
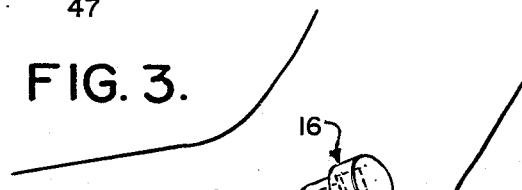
FIG. 3 is a perspective view showing the obturator in its fully inserted position in the cannula.

Referring now to FIG. 3, after venipuncture has been completed and needle 14 removed, the obturator 16 is inserted into the lumen 13 through the distal end thereof. As shown, the length of the obturator 16 is desirably selected such that upon full insertion in lumen 13 the proximal end of the obturator protrudes slightly beyond the proximal end of the cannula, the purpose being to insure that the accumulation of blood or other debris in the lumen 13 is precluded. The obturator 16 serves to obviate the need for an anticoagulant or a continuous infusion during use of the assembly 10. Inasmuch as the obturator 16 remains in the cannula 12 until blood sample is desired, means are preferably provided for releasably retaining the obturator against distal movement in the cannula. A Luer-Lok is preferred for this purpose. Thus, cap 37 preferably comprises an annular member 38 having internal projecting threads 42. When the obturator 16 is fully inserted in the lumen 13 and rotated, the threads 42 engage the flange 26 thereby securing the obturator in place. In this position, plug 39 is fully received in bore 24 thereby completely occluding same.

To effect blood sampling, cap 18 is removed and a syringe 46 or the like is secured to the tubular extension 22, preferably by using a Luer-Lok arrangement. Thus, the proximal end of syringe 46 preferably includes a tubular portion 48 dimensioned for a close fit in the tubular extension 22 and an enlarged annular portion 50 formed about the distal end of the portion 48, the portion 50 having internal projecting threads which mate with flange 23. With the syringe 46 in place, the obturator 16 is partially withdrawn until its proximal end is located distally of the side opening 19 in the cannula 12. This position of obturator 16 may be indicated by a circumferential marking 47 on the obturator which aligns with the distal end of the cannula 12 when the obturator 16 is positioned for sampling. However, the marking 47 may not be necessary as this position of the obturator will also be indicated by the initial accumulation of blood in the syringe. It will be apparent that in this position, obturator 16 still blocks blood flow through the distal end of the cannula 12 and is retained therein by the frictional fit between obturator 16 and lumen 13. Blood may then be withdrawn by aspirating the syringe 46. When sampling is completed, the full length of the obturator 16 is again inserted into the cannula 12 thereby again occluding the lumen 13 and blocking blood flow through the side opening 19. The sampling procedure is completed upon removal of the syringe. Preferably, the cap 18 is replaced.

It will be apparent from the above that additional blood samples may be taken as desired by simply applying a tourniquet, reattaching the syringe 46, and again withdrawing the obturator 16 distally of the side opening 19. When no further samplings are desired, cannula 12 and obturator 16 are simply removed. It is therefore clear that the arrangement described hereinabove readily accommodates multiple blood sampling without the discomfort of repeated venipunctures. Moreover, because the components of the system 10 are inexpensive, they may be discarded after use thereby avoiding resterilization procedures.

Of course, during insertion of the needle 14 in cannula 12, strict sterile techniques should be used. Once the cannula 12 is in place, the needle removed and the obturator partially inserted, blood should be removed from the bore 24 as by using a sterile cotton swab. Thereafter, the bore 24 should be treated with povodine ointments or the like, again as by using a cotton swab. The skin puncture site should be dressed with antibiotics, povodine or the like and sterile gauze bandages applied. The bore of tubular extension 22 should be swabbed and then cleansed as with povodine and alcohol before and after each blood sampling.

Figure 6:
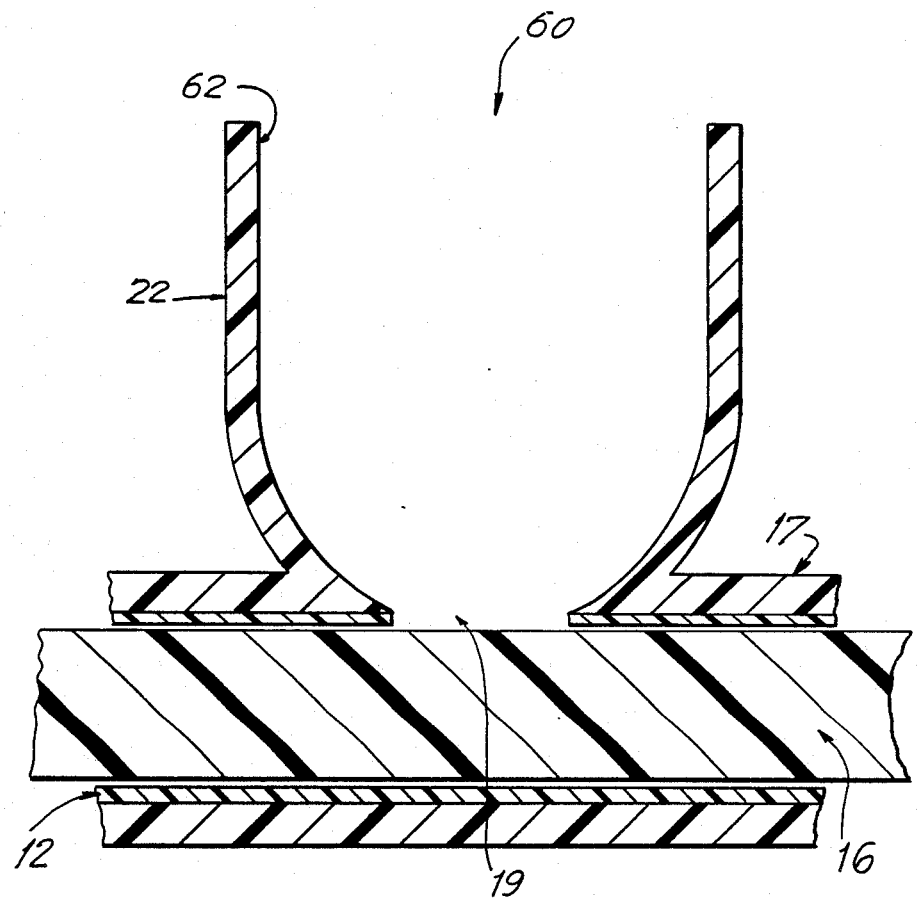
FIG. 6 is a cross-sectional side elevation of the side opening and a portion of the cannula at the side opening location.

It will be appreciated by those skilled in the art that where multiple samplings are to be taken from an indwelling intravascular catheter cleansing of the sideport 19 and the tubular extension 22 between samplings is mandatory. In the preferred assembly 10 of the invention the sideport 19 and the tubular extension 22 may be cleansed between blood samplings under the direct vision of the operator, to assure complete removal of all debris. FIG. 6 is a cross-sectional side elevation of the tubular extension 22 and a portion of the cannula 12. As shown in FIG. 6, the tubular extension 22 and the passageway 60 defined by the tubular extension 22 and leading to sideport 19 are tulip-shaped, narrowing as one approaches the sideport 19. The preferred dimensions of the passageway 60 are about 8 mm in length by about 6 mm in diameter at the mouth 62. One can deviate from these preferred dimensions, but the ratio of the length of the passageway 60 to the diameter of the bore should be less than 2:1.

Penetration of light down the open end of a closed cylinder from generally available ambient light (usually overhead) is such that the depths of the bore can not be visualized unless the ratio of the length of the cylinder to the diameter of the bore of the cylinder is less than 2:1. This is so because a relatively long cylinder tends to transmit essentially only those rays of light which happen to be travelling parallel to the major axis of the cylinder. Only those light rays will penetrate to the depths of the bore. Light rays hitting the open end of the cylinder tangentially will be reflected in various ways depending on the angle of incidence. However, because most materials (e.g. plastics) evidence only a moderate degree of reflectance and also a moderate degree of absorbance of light, the greater the number of reflections necessary, the higher the total fraction of the incident light which will be absorbed. The net result is that the depths of a long narrow cylinder will be shrouded in darkness with the usual conditions of incident light. This would inhibit visual access of the interior of the passageway 60. Without visual access, one cannot be assured of the proper cleanings of the passageway 60 and sideport 19. A proper and thorough cleansing requires direct visualization of the bore of the sideport to its depths. Prior art devices having sideports show tubular extensions with length to diameter ratios of 8:1 or greater.

The tulip-shape of the passageway 60 also facilitates a complete and thorough cleansing of the passageway 60. This tulip shape accomplishes two important objectives. First, it facilitates direct visualization to the depths of the passageway 60 because, aside from the low ratio of length of passageway 60 to diameter of bore, ambient light is reflected off the concave curved sidewalls or "shoulder" back towards the eye of the person using the catheter. The physical or optics advantage of the low length to bore ratio is that incident rays of light from many diverse angles can penetrate directly to the depths of the passageway 60 and be reflected directly back to the eye of the operator using the device (again see FIG. 6). In addition, at sideport 19 in the assembly of the invention tubular extension 22 attaches to the main body of the catheter, substantially perpendicular to it. This is in contrast to prior art devices having sideports where tubular extensions attach to the main body at an acute angle and the walls of the bore are strictly cylindrical with opposite walls parallel at the points of connection with the main body.

This results in an elliptical shaped junctional zone between the tubular extension and the main body of these devices. The forward acute angle thus existing within the bore of such a tubular extension would remain inaccessible to mechanical cleansing by a cotton tipped applicator swab regardless of the amount of axial force applied to the wooden end of the applicator, especially in view of the presence of the fully inserted obturator against which it would abut.

Furthermore, because the end of one cylinder is joined to the side of another in prior art devices it is apparent as well that acute angles inaccessible to cleansing by a cotton tipped applicator swab would exist at the upper and lower edges of the inner bore of the tubular extension where it joins the main body in addition to the inaccessible forward acute angle.

The net result is that regardless of the axial force applied to a cotton tipped applicator swab, a horseshoe shaped peripheral zone of the ellipse will remain inaccessible to cleansing in such devices, especially if combined with a fully inserted occluding obturator. Thus, even if the depths of the bores of acutely angled tubular extensions as in prior art devices were visible, the above described recesses would still remain inaccessible to mechanical cleansing and disinfection with a cotton tipped applicator swab.

In addition to these optics related aspects, the "tulip"-shaped passageway 60, along with its substantially perpendicular disposition in relation to the lumen 13 of the catheter assures that application of pressure to a cotton-tipped applicator swab during cleansing would (1) reach the "shoulder" portion of the passageway 60 where the walls change from parallel to concave curve and (2) tend to produce a "pressure cone" such that the central orifice where the passageway 60 meets the lumen 13 of the main part of the catheter (the central orifice would abut the side of the ensheathed obturator) would be fully mechanically cleansed by the deformation and extrusion of the cotton swab.

While the catheter system 10 has thus far been described in conjunction with intravenous applications, it will be apparent that it may also be utilized in connection with intra-arterial blood sampling. In such event, it will be apparent that due to the elevated arterial pressures, there will likely be some spillage of blood through the distal end of the cannula 12 when the needle 14 is first removed. However, the small amount of blood lost during this initial insertion procedure is generally of no consequence. Therefore, while the system 10 has been described hereinabove in connection with the intravenous applications, it should be understood that it will accommodate intra-arterial applications as well.

Figure 5:
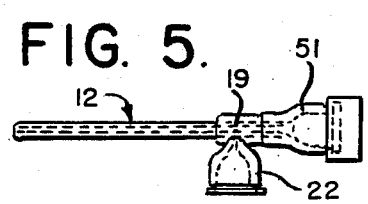
FIG. 5 is an elevational view illustrating the use of a shortened obturator to accommodate continuous intravenous therapy through the side opening.

The system 10, in addition to being particularly suited for accommodating multiple blood sampling, may be readily adapted to accommodate continuous intravenous therapy. Thus, referring to FIG. 5, obturator 16 may be replaced by a shorter obturator 51 which terminates distally of the opening 19 when fully inserted in cannula 12. Obturator 51 may be releasably retained in cannula 12 by utilizing the Luer-Lok arrangement described hereinabove. If an infusion device is then secured to tubular extension 22, again as by using the Luer-Lok arrangement, there will be a continuous flow path into the patient's vein with backflow through the distal end of the cannula being blocked by obturator 51. Continuous intravenous therapy may also be accommodated through the distal end of the cannula 12 by blocking the bore of the tubular extension 22. This may be accomplished, for example, by utilizing the cap 18. Intravenous therapy may then be effected by simply securing the end of the infusion device to the distal end of the cannula 12, again using the Luer-Lok desired.

While I have herein shown and described the preferred embodiments of the present invention and have suggested certain modifications thereto, it will be apparent that further changes and modifications may be made without departing from the spirit and scope of the invention. Accordingly, the above description should be construed as illustrative and not in the limiting sense, the scope of the invention being defined by the following claims.

What is claimed is:

1. A catheter system, which comprises;
    a one-piece cannula defining a continuously extending lumen for accommodating fluid flow, said cannula having an open proximal end, an open distal end, and an opening intermediate said open ends communicating with said lumen, said open distal end of said cannula accommodating cleansing and sterilization thereof;
    an obturator adapted by size and configuration for fully occluding and filling said lumen, slidably inserted in the lumen, said obturator having a distal end and a proximal end, said proximal end being slidably insertable in said lumen through the open distal end thereof, said obturator being movable in said lumen between a first position wherein its proximal end extends proximally of said intermediate opening in which position said obturator fully occludes and fills said lumen for blocking fluid flow between said opening and said proximal end of said cannula, and a second position wherein the obturator proximal end terminates distally of said opening in which position fluid flow through said distal end of said cannula is blocked and fluid flow between said opening and said proximal end of said cannula is unobstructed;
    a valveless member integral with said cannula at said intermediate opening, said member and said cannula thereby defining an integral construction, said member having a member lumen therein having a first end communicating with said opening and a second end open to the outside of the member, said member lumen being tulip-shaped and dimensioned for ready access to accommodate visually observable thorough mechanical cleansing and sterilization thereof as by an antiseptic soaked cotton tip applicator swab when said obturator is in said first position and fluid through said opening is blocked; said member lumen having a length to diameter ratio at the second end of less than 2:1; said member lumen having an axis perpendicular to the cannula lumen; and removable means for closing the second open end of said member lumen.

2. The catheter system according to claim 1, and further comprising means for releasably securing aspiration means to said member for withdrawing fluid in said cannula lumen through said opening.

3. The catheter system according to claim 2, wherein said releasably securing means comprises a Luer-Lok having one mating part secured to said member about said opening and the other mating part secured to said aspiration means.

4. The catheter system according to claim 2, and further comprising means for releasably securing said obturator in said first and second positions.

5. The catheter system according to claim 4, wherein means for releasably securing said obturator in said second position comprises said obturator being dimensioned for a frictional sliding fit in said cannula lumen.

6. The catheter system according to claim 4, wherein said means for releasably securing said obturator in said first position comprises a Luer-Lok having one mating part secured to said distal end of said cannula and the other mating part secured to said distal end of said obturator.

7. The catheter system according to claim 4, and further comprising means for indicating when said obturator is in said second position.

8. The catheter system according to claim 1, and further comprising a venipuncture needle having a distal end and a sharpened proximal end, said sharpened proximal end being removably insertable in said cannula lumen through the distal end thereof to a position wherein said sharpened end projects beyond the proximal end of said cannula.

9. The catheter system according to claim 8, and further comprising a light transmitting hub secured about the distal end of said needle, and wherein said needle defines a continuously extending bore and said hub defines a chamber communicating with said bore.

10. The catheter system according to claim 1, and further comprising means for occluding said opening for accommodating continuous fluid flow through said cannula lumen when said obturator if fully withdrawn therefrom.

11. The catheter system according to claim 10, and further comprising means for occluding the distal end of said cannula lumen for accommodating continuous fluid flow from the proximal end of said cannula lumen through said opening.

* * * * *